United States Patent [19]

Storer et al.

[11] Patent Number: 5,155,112
[45] Date of Patent: Oct. 13, 1992

[54] CYCLOPENTANE DERIVATIVES

[75] Inventors: Richard Storer, Pinner; Ian L. Paternoster, South Harrow; Alan D. Borthwick, London; Keith Biggadike, Greenford, all of England

[73] Assignee: Glaxo Group Limited, London, England

[21] Appl. No.: 617,160

[22] Filed: Nov. 23, 1990

Related U.S. Application Data

[63] Continuation-in-part of Ser. No. 360,537, Jun. 2, 1989, abandoned.

[30] Foreign Application Priority Data

Jun. 3, 1988 [GB] United Kingdom ............... 8813148
Nov. 24, 1989 [GB] United Kingdom ............... 8926623

[51] Int. Cl.$^5$ .................. A61K 31/52; C07D 473/34; C07D 473/16; C07D 473/18
[52] U.S. Cl. .................. 514/262; 514/261; 544/251; 544/276; 544/277
[58] Field of Search .................. 544/251, 276, 277; 514/261, 262

[56] References Cited

U.S. PATENT DOCUMENTS 4,742,064 5/1988 Vince .................. 544/276
4,857,531 8/1989 Borthwick et al. .................. 514/262

OTHER PUBLICATIONS

Jung et al, Helvetica Chimica Act., vol. 66, No. 7, pp. 1915-1921 (1983).

Primary Examiner—Mukund J. Shah
Assistant Examiner—Y. N. Gupta
Attorney, Agent, or Firm—Bacon & Thomas

[57] ABSTRACT

The present invention provides the compounds of formula (I)

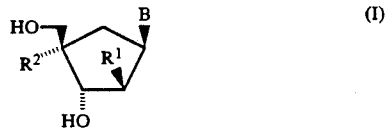

and salts and solvates thereof wherein $R^1$ represents a hydrogen or fluorine atom or a hydroxy group, $R^2$ represents a fluorine atom or a hydroxyl or $C_{1-6}$alkoxy group and B represents a purine base, and describes processes for their preparation, pharmaceutical compositions containing them and their use in the treatment of viral infections, particularly those caused by the Herpetoviridae.

20 Claims, No Drawings

CYCLOPENTANE DERIVATIVES

This is a continuation-in-part application of U.S. Ser. No. 07/360,537, filed Jun. 2, 1989, now abandoned.

This invention relates to new antiviral compounds, to processes for their preparation, to pharmaceutical compositions containing them and to their use in medicine. In particular, the present invention relates to new carbocyclic analogues of nucleosides.

Existing treatments for viral infections include the administration of chemical compounds which are nucleoside analogues, for example 2'-deoxy-5-iodouridine, 9-(2-hydroxyethoxymethyl)guanine and 9-β-D-arabinofuranosyladenine. Carbocyclic analogues of nucleosides are also known to have an effect against certain viruses, and in GB-A-2129425A, GB-A-2179349 and J. Med. Chem. 1984, 27, 1416–21 carbocyclic analogues of nucleosides are disclosed having activity against strains of herpes simplex virus types I and II. There is however a need for compounds with good antiviral activity coupled with lower levels of cytotoxicity.

We have now found that the new carbocylic analogues of nucleosides of formula (I) below have good activity against viruses, especially Herpetoviridae, whilst having a low level of cytotoxicity. Thus, according to one aspect, the present invention provides the compounds of formula (I)

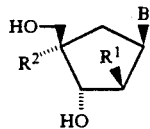

and salts and solvates thereof, in which
  $R^1$ represents a hydrogen or fluorine atom or a hydroxyl group;
  $R^2$ represents a fluorine atom or a hydroxyl or $C_{1-6}$ alkoxy (e.g. methoxy) group; and
  B represents a purine base.

It will be appreciated that, for pharmaceutical use, the salts referred to above will be the physiologically acceptable salts, but other salts may find use, for example in the preparation of compounds of formula (I) and the physiologically acceptable salts thereof.

Suitable physiologically acceptable salts of the compounds of formula (I) include acid addition salts formed with organic or inorganic acids (for example hydrochlorides, hydrobromides, sulphates, phosphates, benzoates, naphthoates, hydroxynaphthoates, p-toluenesulphonates, methanesulphonates, sulphamates, ascorbates, tartrates, salicylates, succinates, lactates, glutarates, glutaconates, acetates, tricarballylates, citrates, fumarates and maleates) and inorganic base salts such as alkali metal salts (for example sodium salts).

It will be understood that the invention includes within its scope biological precursors of the compounds of formula (I) and their physiologically acceptable salts with acids and bases. Biological precursors include for example metabolically labile esters which are converted in vivo into the parent compounds.

The term "purine base" as used herein refers to an unsubstituted or substituted purine wherein the point of attachment is through the 9-position of the purine group. Thus, for example, suitable purine bases include adenin-9-yl, or more particularly guanin-9-yl, 2,6-diaminopurin-9-yl and 2-aminopurin-9-yl.

Compounds of formula (I) in which B represents guanin-9-yl are generally preferred, and a preferred group of compounds of the invention are those of formula (Ia)

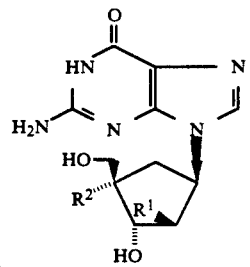

and salts and solvates thereof, in which
  $R^1$ represents a hydrogen or fluorine atom and $R^2$ represents a fluorine atom or a hydroxyl group.

The compounds of the invention may exist in tautomeric forms; for example, the compounds of formula (Ia) may exist in the form

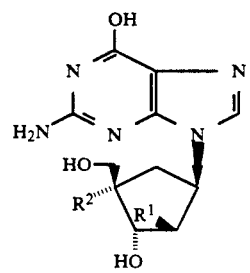

(where $R^1$ and $R^2$ are as defined in formula (Ia) above). It will be understood that all tautomeric forms of the compounds of formulae (I) and (Ia) are included within the scope of the invention.

It will be further understood that the present invention encompasses the individual enantiomers of the compounds of formulae (I) and (Ia) and their tautomers as well as wholly or partially racemic mixtures of such enantiomers.

The compounds of formula (I) in which B represents guanin-9-yl, $R^1$ represents hydrogen and $R^2$ represents hydroxyl and their physiologically acceptable salts and solvates are particularly preferred, especially the 1'S, 3'S, 4'S enantiomer thereof, namely (1'S, 3'S, 4'S)-2-amino-1,9-dihydro-9-[3,4-dihydroxy-3-hydroxymethyl-1-cyclopentyl]-6H-purin-6-one and physiologically acceptable salts and solvates thereof (e.g. the hydrochloride or sodium salt thereof).

A particularly preferred compound of the present invention is (1'S,3'S,4'S)-2-amino-1,9-dihydro-9-[3,4-dihydroxy-3-hydroxymethyl-1-cyclopentyl]-6H-purin-6-one, sodium salt.

We have found that compounds of the invention are highly potent in vitro and in vivo against strains of both herpes simplex virus type I and herpes simplex virus type II whilst having a low level of cytotoxicity. In vitro testing was carried out using the standard plaque reduction test whilst in vivo testing was carried out on the mouse according to the method described by Ericson et. al. (1985) Antimicrobial Agents-Chemotherapy 27, 753–759.

It should be noted that the compounds of formula (I) lack a glycosidic bond which forms a site for both chemical and biological cleavage. Stability against glycosidic cleavage is, of course, a valuable feature in compounds for in vivo use.

In view of their antiviral activity, the compounds according to the invention and their physiologically acceptable salts and solvates recommend themselves for the treatment of a variety of diseases caused by viruses, particularly primary and recurrent infections caused by the Herpetoviridae in human beings and animals. Such diseases include stomatitis, skin eruptions, shingles, encephalitis, eye and genital herpes infections, retinitis and pneumonitis.

The invention accordingly provides the compounds of formula (I) and their physiologically acceptable salts and solvates for use in human and veterinary medicine, more particularly for use in the therapy or prophylaxis of viral infections, especially Herpetoviridae (e.g. herpes simplex) infections, in a human or animal subject.

According to a further aspect of the invention we provide the use of a compound of formula (I) or a physiologically acceptable salt or solvate thereof for the manufacture of a medicament for the therapy or prophylaxis of viral infections, especially primary and recurrent infections caused by the Herpetoviridae in human beings and animals.

According to a yet further aspect of the invention we provide a method of treatment of the human or non-human animal body to combat viruses, especially the Herpetoviridae, which method comprises administering to the body an effective amount of a compound of formula (I) or a physiologically acceptable salt or solvate thereof.

The compounds according to the invention may be formulated for administration in any convenient way, and the invention thereof also includes within its scope pharmaceutical compositions for use in the therapy or prophylaxis of viral infections, especially Herpetoviridae (e.g. herpes simplex) infections, in a human or animal subject comprising a compound of formula (I) or a physiologically acceptable salt or solvate thereof together, if desirable, with one or more physiologically acceptable carriers or excipients.

The compounds according to the invention may, for example, be formulated for oral, buccal, parenteral, topical or rectal administration.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, sugar, maize-starch, calcium phosphate or sorbitol; lubricants, for example, magnesium stearate, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives (such as suspending agents), for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan monooleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The compound may also be formulated as suppositories, e.g. containing conventional suppository bases such as cocoa butter or other glycerides.

For buccal administration the compositions may take the form of tablets or lozenges formulated in conventional manner.

The compound according to the invention may also be formulated for injection and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or toxicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

For topical administration the compound according to the invention may be formulated as ointments, creams, lotions, powders, pessaries, sprays, aerosols or drops (e.g. eye or nose drops). Ointments and creams may, for example, be formulated with an aqueous or oily base with the addition of suitable thickening and/or gelling agents. Such bases may thus, for example, include water and/or an oil such as liquid paraffin or a vegetable oil such as arachis oil or castor oil. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Aerosol sprays are conveniently delivered from pressurised packs, with the use of a suitable propellant, e.g. dichlorodifluoromethane, trichlorofluoromethane, dichlorotetrafluoroethane, carbon dioxide or other suitable gas.

The pharmaceutical compositions according to the invention may also contain other active ingredients such as antimicrobial agents, or preservatives.

The compositions may contain from 0.1%–99% of the active material. For topical administration, for example, the composition will generally contain from 0.01% to 20%, more preferably 0.5% to 5% of the active material.

For topical administration the daily dosage as employed for adult human treatment will range from 0.1 mg to 1000 mg, preferably 0.5 mg to 10 mg. However, it will be appreciated that extensive skin infections may require the use of higher doses.

For systemic administration the daily dosage as employed for adult human treatment will range from 5 mg to 5000 mg, preferably 50 mg to 2000 mg, which may be administered in 1 to 5 daily doses, for example, depending on the route of administration and the condition of the patient. When the compositions comprise dosage units, each unit will preferably contain 2 mg to 2000 mg of active ingredient, for example 50 mg to 500 mg. For serious infections the compound may be administered by intravenous infusion using, for example 0.01 to 10 mg/kg/hr of the active ingredient.

The compounds of the invention may be administered in combination with one or more further therapeutic agents such as a different antiviral agent.

Suitable methods for preparing compounds of formula (I) are described below; the groups B, $R^1$ and $R^2$ are as defined above except where otherwise indicated. It will be appreciated that the following reactions may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g. benzyl), acyl or aryl (e.g. 2,4-dinitrophenyl); subsequent removal of the protecting group being effected when desired by hydrolysis or hydrogenolysis as appropriate using standard conditions. Hydroxyl groups may be protected using any conventional hydroxyl protecting group, for example, as described in 'Protective Groups in Organic Chemistry', Ed. J. F. W. McOmie (Plenum Press, 1973) or 'Protective Groups in Organic Synthesis' by Theodora W. Greene (John Wiley and Sons, 1981). Examples of suitable hydroxyl protecting groups include groups selected from alkyl (e.g. methyl, t-butyl or methoxymethyl), aralkyl (e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyldimethylsilyl). The hydroxyl groups at the 3'-and 5'-positions may together be protected by a single protecting group such as a disiloxanyl group (e.g. a tetraalkyldisiloxanyl group such as 1,1,3,3-tetraisopropyldisilox-1,3-diyl) or benzylidene group. The hydroxyl protecting groups may be removed by conventional techniques. Thus, for example, alkyl, silyl, acyl and heterocyclic groups may be removed by solvolysis, e.g. by hydrolysis under acidic or basic conditions. Aralkyl groups such as triphenylmethyl may similarly be removed by solvolysis, e.g. by hydrolysis under acidic conditions. Aralkyl groups such as benzyl may be cleaved by hydrogenolysis in the presence of a noble metal catalyst such as palladium-on-charcoal. Silyl groups, including disiloxanyl groups, may also conveniently be removed using a source of fluoride ions such as tetra-n-butylammonium fluoride.

According to another aspect of the present invention, we provide processes for the preparation of compounds of formula (I). Thus, one process (A) for the preparation of compounds of formula (I) in which B represents guanin-9-yl comprises reacting a compound of formula (II)

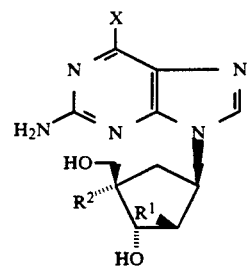

(wherein X represents an atom or group convertible to a hydroxyl group) or a salt thereof to convert the atom or group X to a hydroxyl group.

X may represent, for example, an atom or group convertible by hydrolysis to a hydroxyl group. Suitable possibilities for X include halogen (e.g. chlorine), $NH_2$, alkoxyamino (e.g. $CH_3ONH-$), alkoxy (e.g. methoxy), and in particular phenylmethoxyamino ($PhCH_2ONH-$).

It will be appreciated that the resulting compounds in which X is a hydroxyl group are merely tautomers of the compounds of formula (I) in which B represents guanin-9-yl.

The hydrolysis may conveniently be effected in water or a mixture of water and a suitable water-miscible solvent such as an alcohol (e.g. methanol or ethanol), an ether (e.g. dioxan or tetrahydrofuran), a ketone (e.g. acetone), an amide (e.g. dimethylformamide) or a sulphoxide (e.g. dimethylsulphoxide). The reaction conveniently takes place in the presence of an acid or base. Suitable acids include organic acids (e.g. p-toluenesulphonic acid) and inorganic acids (e.g. hydrochloric acid, nitric acid or sulphuric acid). In some cases the acid may also be used as the reaction solvent, especially when the acid used is hydrochloric acid. Suitable bases include inorganic bases (e.g. alkali metal hydroxides or carbonates such as sodium hydroxide, potassium hydroxide, sodium carbonate or potassium carbonate). Hydrolysis is conveniently effected at a temperature in the range of $-10°$ to $+150°$ C., e.g. $+50°$ to $+120°$ C.

When X in formula (II) represents alkoxylamine (e.g. $CH_3ONH-$) the conversion of X to a hydroxyl group may also be effected by reaction with adenosine deaminase, optionally preceded by reaction with a suitable reducing agent such as aluminium amalgam.

The reduction may conveniently be carried out in an ether solvent (e.g. tetrahydrofuran) optionally also containing water and at room temperature.

The adenosine deaminase may conveniently be added to a solution of a compound of formula (II) in which X is alkoxylamine or the product of the reduction reaction (i.e. a compound of formula (II) in which X is $NH_2$) in phosphate buffer (e.g. pH 7.5 phosphate buffer).

Another process (B) for preparing compounds of formula (I) in which $R^2$ is a hydroxyl group comprises reacting a compound of formula (III)

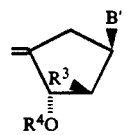

(wherein $R^3$ is as defined for $R^1$ in formula (I) or $R^3$ is a group $OR^4$ and $R^4$ is a hydrogen atom or a hydroxyl protecting group and B' is a group B or is a protected purine base) or a salt thereof under oxidising conditions and thereafter removing any protecting groups present.

The oxidation may conveniently be effected using any suitable oxidising agent such as osmium tetroxide in an appropriate solvent (e.g. pyridine). The oxidation may be carried out at any convenient temperature, preferably at ambient temperature.

The oxidation reaction produces the desired compounds of formula (I) and protected derivatives thereof together with compounds of formula (IV)

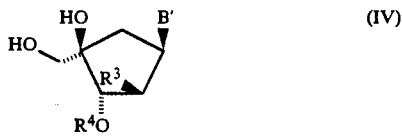

(wherein $R^3$, $R^4$ and B' are as defined above) or a salt thereof. The compounds of formula (IV) and the desired isomeric compounds of formula (I) and protected derivatives thereof may be separated using conventional separation techniques. Thus, for example, the separation may be effected using chromatography, e.g. silica gel chromatography or preparative layer chromatography.

Another process (C) for preparing compounds of formula (I) in which $R^2$ is a fluorine atom comprises reacting a compound of formula (V)

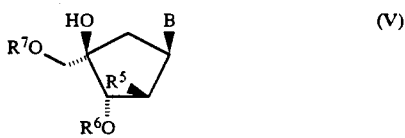

(wherein $R^5$ is a hydrogen or fluorine atom or a group $OR^8$ and $R^6$, $R^7$ and $R^8$ are suitable hydroxyl protecting groups) or a salt thereof with a fluorinating agent followed by removal of the protecting groups present.

Suitable fluorinating agents include diethylaminosulphur trifluoride (DAST) or diethyl-(2-chloro-1,1,2-trifluoroethyl)amine. The reaction is conveniently effected in an inert solvent such as a halogenated hydrocarbon, e.g. dichloromethane or chloroform or an ether, e.g. tetrahydrofuran, and at a temperature of, for example, from −70° to 0° C. Alternatively, the reaction may be effected using hydrogen fluoride in pyridine or triethylamine.

The compounds of formula (V) are conveniently prepared from compounds of formula (IV) using standard means of hydroxyl group protection.

Another process (D) for the preparation of compounds of formula (I) in which $R^2$ is hydroxy comprises reacting a compound of formula (VI)

(wherein $R^5$, $R^6$ and $R^7$ are as defined previously and L represents a suitable displaceable atom or group) or a salt thereof with a purine derivative B'H (where B' is as defined previously) or a salt thereof.

L may represent, for example, a conventional leaving group such as a group $OSO_2R^9$ where $R^9$ is an alkyl (e.g. methyl), haloalkyl (e.g. trifluoromethyl) or aryl (e.g. tolyl) group.

The displacement reaction may conveniently be effected in a suitable solvent such as a sulphoxide (e.g. dimethylsulphoxide) and preferably in the presence of base such as an alkali metal carbonate (e.g. potassium carbonate). The reaction may, for example, be effected at a temperature in the range of 20° to 150° C.

Another process (E) for the preparation of compounds of formula (I) comprises removing one or more amino and/or hydroxyl protecting groups from a suitably protected derivative of a compound of formula (I). Suitable protecting groups and conditions for their removal will be familiar to the skilled chemist but will include groups and conditions described above.

Compounds of formula (II) may be prepared from compounds of formula (VII)

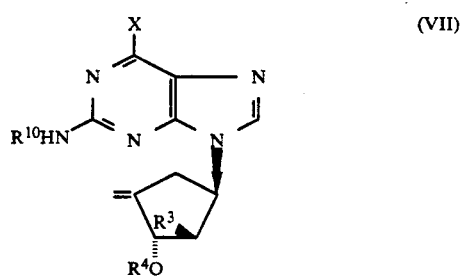

(wherein $R^3$, $R^4$ and X are as defined previously and $R^{10}$ is a hydrogen atom or a protecting group) by oxidation under the conditions of process (B) (in the preparation of compounds of formula (II) in which $R^2$ is hydroxy) followed by fluorination under the conditions of process (C) (in the preparation of compounds of formula (II) in which $R^2$ is fluorine) and thereafter followed by removal of any protecting groups present.

Alternatively, compounds of formula (II) in which $R^2$ is hydroxy may be prepared from compounds of formula (VII) by epoxidation of the double bond, for example using a peroxide such as tert-butyl hydroperoxide, followed by standard epoxide ring opening to form the diol (i.e. a compound of formula (II) in which $R^2$ is hydroxy or a protected derivative thereof) and thereafter followed by removal of any protecting groups present. When tert-butyl hydroperoxide is used to effect epoxidation the epoxidation reaction is conveniently carried out in the presence of a vanadium catalyst (e.g. vanadyl acetylacetonate) in a suitable solvent such as a halogenated hydrocarbon (e.g. dichloromethane) at an elevated temperature, e.g. reflux.

Compounds of formula (II) in which X represents alkoxyamino (e.g. $CH_3ONH-$) or phenylmethoxyamino may also be prepared from compounds of formula (VIII)

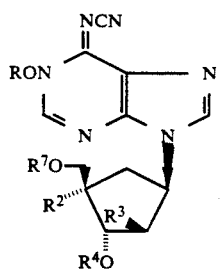

(VIII)

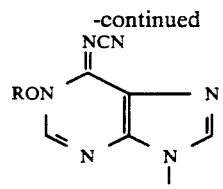

(iii)

previously defined) by iodination, for example, using a suitable iodinating agent to give the corresponding iodo compound (XI)

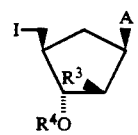

(XI)

(wherein $R^3$, $R^4$ and $R^7$ are as defined previously and R is an alkyl group, e.g. methyl or benzyl) by heating, e.g. at reflux, in a suitable solvent such as an alcohol (e.g. ethanol) or a mixture of water and an alcohol (e.g. aqueous ethanol) and in the presence of a suitable base (e.g. 1,8-diazabicyclo[5.4.0]undec-7-ene or an alkali metal hydrogen carbonate such as potassium hydrogen carbonate) followed by removal of any protecting groups present.

Compounds of formula (VIII) may be prepared from compounds of formula (IX)

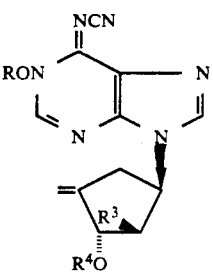

(IX)

(wherein $R^3$, $R^4$ and R are as defined previously) according to the general conditions described above for the preparation of compounds of formula (II) from compounds of formula (VII) and thereafter followed by protection to introduce the $R^7$ group if necessary.

Compounds of formula (III), (VII) and (IX) may be prepared from an appropriate compound of formula (X)

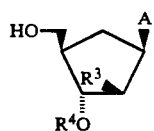

(X)

(wherein $R^3$ and $R^4$ are as defined previously and A represents a group

B, (i)

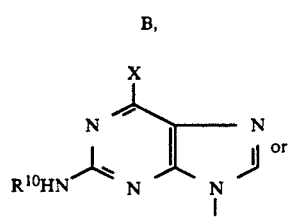

or (ii)

and thereafter reacting said iodo compound (XI) to give the desired intermediate (III), (VII) or (IX).

Suitable iodinating agents include phosphonium iodides (e.g. methyl triphenoxyphosphonium iodide) and the iodination reaction may conveniently be effected at a temperature in the range of $-70°$ to $+20°$ C. in a suitable solvent such as an ether (e.g. tetrahydrofuran) or an amide (e.g. dimethylformamide).

Conversion of (XI) to the appropriate alkene may be effected by heating (XI), e.g. at a temperature in the range 50° to 80° C., in a suitable solvent such as pyridine and optionally in the presence of a base (e.g. 1,5-diazabicyclo[4.3.0]non-5-ene).

Compounds of formula (X) in which $R^3$ represents a group $OR^4$ and A represents group (i) or (ii) are either known compounds or may be prepared by methods analogous to those used to prepare the known compounds of formula (X). Similarly, compounds of formula (X) in which $R^3$ represents fluorine and A represents group (i) or (ii) are either known compounds described in GB-A-2179349 or may be prepared by methods analogous to those used to prepare the known compounds.

Compounds of formula (X) in which A represents group (iii) may be prepared from compounds of formula (XII)

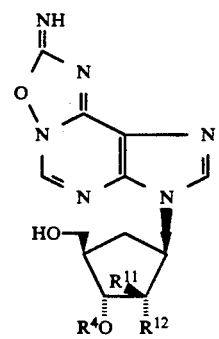

(XII)

(wherein $R^4$ is as defined previously, $R^{11}$ represents $R^3$ and $R^{12}$ represents a hydrogen atom or $R^{11}$ represents a hydrogen atom and $R^{12}$ represents a hydroxyl group) by adding a suitable base such as a tertiary amine (e.g. triethylamine) to a solution of a compound (XII) in a solvent such as an amide (e.g. dimethylformamide) and thereafter treating the mixture with an alcohol ROH (where R is as previously defined), followed, where necessary, by conversion of the 2'-α-OH group to a hydrogen atom, a 2'-β-fluorine atom or a 2'-β-OH group as described hereinafter.

Compounds of formula (XII) may be prepared from compounds of formula (XIII)

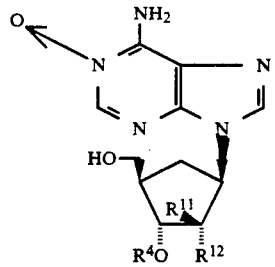
(XIII)

(wherein $R^4$, $R^{11}$ and $R^{12}$ are as defined previously) by reaction with cyanogen bromide in a solvent such as an alcohol (e.g. methanol) at reduced temperature, e.g. −50° to 0° C., followed, if desired, by conversion of the 2'-α-OH group (where present) to a hydrogen atom, a 2'-β-fluorine atom or a 2'-β-OH group as described hereinafter.

Compounds of formula (XIII) may be prepared from the known compound aristeromycin by oxidation, for example using a peracid such as m-chloroperbenzoic acid. The aristeromycin 2'-α-OH group may, if desired, be converted to a hydrogen atom, a 2'-β-fluorine atom or a 2'-β-OH group either prior to or subsequent to the oxidation using the methods described hereinafter.

Compounds of formula (VI) (e.g. in which L is $OSO_2R^9$) may be prepared from compounds of formula (XIV)

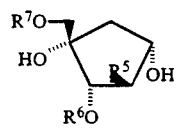
(XIV)

(wherein $R^5$, $R^6$ and $R^7$ are as defined previously), for example, by sulphonation with a suitable sulphonyl halide $R^9SO_2Hal$ (where $R^9$ is as defined previously and Hal is a halogen atom, e.g. chlorine).

Compounds of formula (XIV) in which $R^5$ is a fluorine atom may be prepared from compounds of formula (XV)

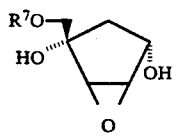
(XV)

(wherein $R^7$ is as defined previously) or a hydroxyl group protected derivatived thereof by fluorination using a suitable fluorinating agent such as potassium hydrogen difluoride followed by protection of the free hydroxyl group at the 3'-position. Compounds of formula (XIV) in which $R^5$ is a group $OR^8$ may be prepared from compounds of formula (XV) by hydrolysis followed, if necessary, by inversion of the 2'-OH group using the method described hereinafter and thereafter treating the 2'-β-OH group with a protecting group Compounds of formula (XV) may be prepared from compounds of formula (XVI)

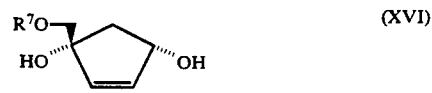
(XVI)

(wherein $R^7$ is as defined previously) by oxidation using a suitable peroxide oxidising agent such as t-butyl hydroperoxide in the presence of a vanadium catalyst (e.g. vanadyl acetylacetonate).

Compounds of formula (XVI) may be prepared from compounds of formula (XVII)

(XVII)

under suitable hydroxylating conditions.

Compounds of formula (XVII) may be prepared from cyclopentadiene by alkylation using a reagent $R^7OCH_2$-Hal (where $R^7$ and Hal are as defined previously).

The compound of formula (IX) in which R represents benzyl and $R^3$ and $R^4$ represent hydrogen atoms may also be prepared from the compound of formula (XVIII)

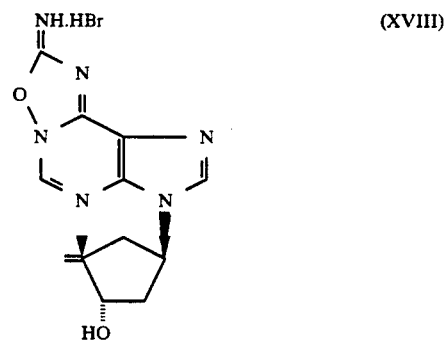
(XVIII)

by adding a suitable base such as a tertiary amine (e.g. triethylamine) to a solution of the compound (XVIII) and a benzyl halide (e.g. benzyl bromide) in a solvent such as an amide (e.g. dimethylformamide) and allowing the reaction to proceed at about ambient temperature.

The compound of formula (XVIII) may be prepared from the compound of formula (XIX)

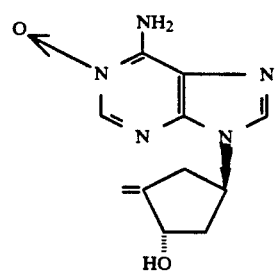
(XIX)

by reaction with cyanogen bromide in a solvent such as an alcohol (e.g. methanol) at reduced temperature, e.g. −50° to 0° C.

The compound of formula (XIX) may be prepared from the compound of formula (XX)

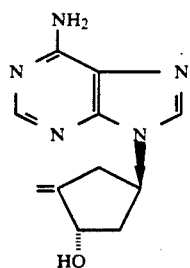

by oxidation, for example using a peracid such as m-chloroperbenzoic acid. The reaction is conveniently effected in a suitable solvent such as an alcohol (e.g. ethanol) at about ambient temperature.

The compound of formula (XX) may be prepared from compounds of formula (XXI)

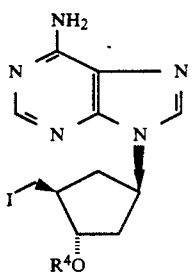

(wherein $R^4$ is a suitable acyl group as defined below) by heating the compound (XXI), e.g. at a temperature of about 80° C. in a suitable solvent such as pyridine and optionally in the presence of a base (e.g. 1,5-diazabicyclo[4.3.0]non-5-ene), followed by removal of the protecting group $R^4$. $R^4$ represents an acyl group such as benzoyl which may be removed using an ion exchange resin such as Amberlite 1RA 400(OH).

Compounds of formula (XXI) may be prepared by iodination of a compound of formula (XXII)

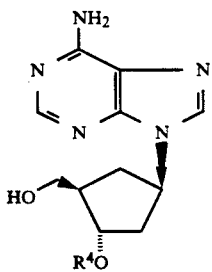

(wherein $R^4$ is an acyl group as defined previously). Suitable iodinating agents include phosphonium iodides (e.g. methyl triphenoxyphosphonium iodide) and the iodination reaction may conveniently be effected at a temperature in the range of $-70°$ C. to $+20°$ C. in a suitable solvent such as an ether (e.g. tetrahydrofuran) or an amide (e.g. dimethylformamide).

Compounds of formula (XXII) may be prepared from aristeromycin by conversion of the 2'-α-OH group to a hydrogen atom and the introduction of the $R^4$ protecting group according to the general methods described herein. This may conveniently be achieved by initially protecting the aristeromycin 5'—OH group, for example as a silyl ether by reaction with a silyl halide such as a trialkylsilyl halide (e.g. t-butyldimethylsilyl chloride or thexyldimethylsilyl-chloride). The $R^4$ protecting group may then conveniently be introduced by treating the silylated intermediate with n-dibutyltin oxide and then with an acyl halide $R^4$Hal (where Hal is a halogen atom, e.g. chlorine).

It should be appreciated that compounds unsubstituted at the 2'-position or substituted at the 2'-position by a 2'-β-fluorine atom or a 2'-β-hydroxyl group may be prepared at any suitable stage in the overall reaction sequence from corresponding compounds containing a 2'-α-hydroxy substituent. Conversion of a 2'-α-hydroxy compound to a 2'-β-fluoro compound may be effected using the general conditions described in process (C) above. Replacement of a 2'-α-hydroxy substituent by a hydrogen atom may be effected by converting the hydroxyl group to a leaving group removable by reduction (e.g. by homolytic reduction) and thereafter reducing the aforesaid compound using, for example, an alkyltin hydride (e.g. tri-n-butyltin hydride) in the presence of a radical initiator such as a peroxide, 2,2'-azobis(2-methylpropionitrile) or light. Suitable leaving groups include —OC(=S)OR$^{13}$ (where R$^{13}$ is $C_{1-6}$alkyl, aryl such as phenyl, heteroaryl such as imidazole or $C_{1-6}$alkylaryl such as p-tolyl). Conversion of the hydroxyl group to —OC(=S)OR$^{13}$ may be effected using, for example, aryl halothionoformates such as phenyl chlorothionocarbonate in the presence of a suitable base such as an amine (e.g. pyridine or 4-dimethylaminopyridine) and in a solvent such as a halogenated hydrocarbon (e.g. dichloromethane). Conversion of a 2'-α-hydroxy compound to a 2'-β-hydroxy compound may be effected by converting the hydroxyl group to a suitable leaving group L as defined hereinabove and then displacing the group L with an oxygen nucleophile with inversion of configuration. This nucleophilic substitution is a very well-known reaction and suitable conditions to effect the desired conversion will be familiar to the skilled chemist.

It will, of course, be recognised that other hydroxyl groups present in the starting material may need to be protected prior to reaction at the 2'-position. Suitable protecting groups and conditions for their removal will be familiar to the skilled chemist but will include groups and conditions described hereinabove.

When a compound of the invention or an intermediate is required having $R^2$ as a $C_{1-6}$alkoxy (e.g. methoxy) group, such compounds may be prepared from corresponding compounds in which $R^2$ is a hydroxyl group using standard etherifying conditions. Again it will be recognised that other hydroxyl groups present in the starting material may need to be protected prior to the etherification reaction.

It will be appreciated that compounds prepared from the starting material aristeromycin will be chiral. When a specific enantiomer of formula (I) is required, this may be prepared from a suitable chiral intermediate or, alternatively, by resolution of the corresponding racemate of formula (I) using conventional methods.

Inorganic basic salts of compounds of the invention may be prepared by reacting the corresponding free base with a suitable base (e.g. a hydroxide such as sodium hydroxide) in a suitable solvent (e.g. water).

Acid addition salts of compounds of the invention may be prepared by treating the corresponding free base with a suitable acid using conventional methods. Physiologically acceptable acid addition salts may be prepared by reacting the free base of a compound of formula (I) with a suitable acid in the presence of a solvent such as an ester (e.g. ethyl acetate) or an alcohol (e.g. methanol, ethanol or isopropanol).

Physiologically acceptable salts may also be prepared from other salts, including other physiologically acceptable salts, of compounds of formula (I) using conventional ion exchange methods.

It will be appreciated that many of the intermediates described herein are novel compounds [for example, compounds of formulae (II), (IV), (V), (VI), (VIII), (XV) and (XVI)] and it should be understood that all such novel compounds form further aspects of this invention.

The following Preparations and Examples illustrate the present invention but should not be construed as a limitation of the invention. All temperatures are in °C.

INTERMEDIATE 1

(±)(1α,2β,3α,4α)-4-(2-Amino-6-methoxy-9H-purin-9-yl)-3-fluoro-2-hydroxycyclopentanemethanol (±)(1α,2β,3α,4α)-4-(2-Amino-6-chloro-9H-purin-9-yl)-3-fluoro-2-hydroxycyclopentanemethanol[1] (2 g) was added to a solution of sodium (457 mg) in methanol (25 ml) and the mixture stirred at 50° for 1.5 h. The solution was cooled and neutralised with DOWEX 50W×8 resin (H+, 6.25 g). The resin was removed by filtration and the filtrate was evaporated to a foam. This material was purified by silica gel chromatography (Merck Kieselgel 60) using 5:1 ethyl acetate:ethanol as eluting solvent to give, after trituration with methanol, the title compound as white crystals (1.37 g). $^1$H nmr (DMSO-d$_6$) δ 7.90(1H), 6.47(2H), 5.43(1H), 4.7–5.0(3H), 4.0(1H), 3.95(3H), 3.52(2H), 2.32(1H) and 1.95–2.15(2H).

1. Intermediate 15 in GB-A-2179349.

INTERMEDIATE 2

(±)(1α,2β,3β,5β)-3-(2-Amino-6-methoxy-9H-purin-9-yl)-5-((tert-butyldimethylsilyl)oxy)methyl-2-fluorocyclopentanol.

Intermediate 1 (3.56 g) was added to a stirred solution of tert-butyl dimethylsilyl chloride (1.98 g) and imidazole (3.26 g) in dry N,N-dimethylformamide (20 ml). After 1 h the mixture was partitioned between water (100 ml) and ethyl acetate (100 ml). The organic phase was separated, combined with a second ethyl acetate extract (25 ml), washed with water (3×50 ml), dried and evaporated to a cream solid. Trituration of this material with ether provided the title compound as white crystals (4.18 g), mp 87°–90°. $^1$H nmr (DMSO-d$_6$) 7.79(1H), 6.39(2H), 5.39(1H), 4.6–4.9(2H), 3.92(1H), 3.88(3H), 3.63(2H), 2.24(1H) and 1.97(2H).

INTERMEDIATE 3

(±)(1'α,2'α,3'β,4'α)-9-4-((tert-Butyldimethylsilyl)oxy)-methyl-2-fluoro-3-triphenylmethoxy-1-cyclopentyl-6-methoxy-2-triphenylmethylamino-9H-purine A mixture of Intermediate 2 (2.91 g), triphenylmethyl chloride (5.91 g) and powdered molecular sieves (4A, 30 g) was heated under reflux in dichloromethane (250 ml) for 3 days. More triphenylmethyl chloride (1.77 g) was then added and the mixture heated under reflux for a further 24 h and then filtered. Evaporation of the filtrate left a yellow foam which was purified by silica gel chromatography (Merk Kieselgel 60) using initially 2:1 ether:petrol and finally ether as eluting solvent to give the title compound as a pale yellow foam (5.21 g).

λ$_{max}$(ethanol) 258.4 nm (E$_1^1$144), 285 nm (E$_1^1$ 123), $^1$H nmr (DMSO-d$_6$, 60°) δ 7.6(1H), 7.1–7.5(30H), 6.98(1H), 4.57(1H), 3.9(1H), 3.77(1H), 3.65(3H), 3.45–3.65(2H), 2.5(1H), 2.15(1H), 1.86(1H), 0.83(9H), −0.02(3H) and −0.06(3H).

INTERMEDIATE 4

(±)(1α,2β,3α,4α)-3-Fluoro-4-(6-methoxy-2-triphenylmethylamino-9H-purin-9-yl)-2-triphenylmethyoxycyclopentanemethanol 1M Tetra-n-butylammonium fluoride in tetrahydrofuran (0.2 ml) was added to a solution of Intermediate 3 (175 mg) in the same solvent (2 ml). After 30 min the solvent was evaporated and the residue was partitioned between water (5 ml) and ethyl acetate (5 ml). The organic phase was separated, washed with water (5 ml) and dried and evaporated to a yellow foam. Purification by silica gel chromatography (Merck Kieselgel 60) using ethyl acetate as eluting solvent followed by recrystallisation from ether afforded the title compound as colourless crystals (84 mg), mp 220°–222°. $^1$H nmr (DMSO-d$_6$, 60°) 7.64(1H), 7.1–7.5(30H), 7.02(1H), 4.4–4.7(2H), 3.86(1H), 3.64(3H), 3.62(1H), 3.15–3.45(2H), 2.5(1H), 2.16(1H) and 1.82(1H).

INTERMEDIATE 5

(±)(1'α,2'α,3'β,4'α)-9-2-Fluoro-4-iodomethyl-3-triphenylmethoxy-1-cyclopentyl-6-methoxy-2-triphenylmethylamino-9H-purine.

Methyl triphenoxyphosphonium iodide (3.73 g) was added to a stirred and cooled (−65°) solution of Intermediate 4 (4.3 g) in dry tetrahydrofuran (100 ml). The mixture was allowed to warm to 0° over 1.5 h when methanol (0.25 ml) was added and the solution was evaporated to an orange foam which was partitioned between water (75 ml) and ether (125 ml). The organic phase was separated, washed with water (40 ml), dried and evaporated and the residue purified by silica gel chromatography (Merck Kieselgel 60) using 1:1 ethyl acetate:hexane as eluting solvent. The title compound was obtained as a cream foam (4.8 g) a sample of which was crystallised from ethyl acetate to give pale yellow crystals, mp 230°–233°. $^1$H nmr (DMSO-d$_6$) δ 7.72(1H), 7.15–7.55(30H), 7.04(1H), 4.64(1H), 4.32(1H), 3.78(1H), 3.66(3H), 2.9–3.15(2H), 2.15–2.55(2H) and 1.78(1H).

INTERMEDIATE 6

(±)(1'α,2'α,3'β)-9-2-Fluoro-4-methylene-3-triphenylmethoxy-1-cyclopentyl-6-methoxy-2-triphenylmethylamino-9H-purine A solution of Intermediate 5 (180 mg) and 1,5-diazabicyclo-[4.3.0]non-5-ene (37 mg) in pyridine (2.4 ml) was stirred at 55° for 3 h. The solvent was then evaporated and the residue partitioned between water (5 ml) and ethyl acetate (5 ml). The organic phase was separated, washed successively with 0.1N hydrochloric acid, brine and water and dried and evaporated to a yellow foam. Purification by preparative layer chromatography (Whatman silica) using 1:1 ethyl acetate:petrol for development gave the title compound as a white foam (74 mg) a sample of which was crystallised from ether to afford colourless crystals, mp 267°–268°. $^1$H nmr (DMSO-d$_6$, 60°) δ 7.7(1H), 7.1–7.5(30H), 7.02(1H), 5.25(1H), 5.15(1H), 4.73(1H), 4.37(1H), 4.0(1H), 3.63(3H) and 2.8(2H).

INTERMEDIATE 7

(±)(1α,2α,3β,4β) and (1α,2β,3α,4α)-3-Fluoro-1-hydroxy-4-(6-methoxy-2-triphenylmethylamino-9H-purin-9-yl)-2-triphenylmethoxycyclopentane-methanol A solution of osmium tetroxide (100 mg) in pyridine (1 ml) was added to a solution of Intermediate 6 (300 mg) in the same solvent (2 ml). After 1.5 h a solution of sodium metabisulphite (300 mg) in water (1 ml) was added and the mixture stirred for a further 18 h. The orange supernatant was decanted and partitioned between water (5 ml) and ethyl acetate (5 ml). The organic phase was separated, washed with water and dried and evaporated to give a mixture of the title isomers as a white foam (325 mg). Preparative layer chromatography (Whatman silica) using 15:1 chloroform:ethanol for development provided the less polar 1α,2α,3β,4β-isomer as a colourless glass, $^1$H nmr (DMSO-$d_6$, 60°) δ 7.52(1H), 7.1–7.5(30H), 6.94(1H), 4.88(1H), 4.4–4.75(2H), 4.13(1H), 3.97(1H), 3.45(3H), 3.1–3.3(2H), 2.32(1H) and 1.93(1H); and the more polar 1α,2β,3α,4α-isomers as white crystals, mp 201°–3°, $^1$H nmr (DMSO-$d_6$, 60°) δ 7.63(1H), 7.1–7.5(30H), 6.97(1H), 4.9(1H), 4.61(1H), 4.15(1H), 3.87(1H), 3.8–3.9(2H), 3.45(3H), 3.15(1H), 2.4–2.5(1H) and 2.17(1H).

INTERMEDIATE 8

(±)(1α,2α,3β,4β) and (1α,2β,3α,4α)-3-Fluoro-4-6-methoxy-2-triphenylmethylamino-9H-purin-9-yl-2-triphenylmethoxy-1-triphenylmethoxymethylcyclopentanol A ca 6:4 mixture of the isomers of Intermediate 7 (622 mg) was treated with triphenylmethyl chloride (272 mg) in dichloromethane (30 ml) containing powdered molecular sieves (4A, 3 g) for 3 days. The mixture was filtered and the filtrate evaporated to provide a mixture of the title isomers as a white foam (830 mg). Separation by silica gel chromatography (Merck Kieselgel) using 4:1 ether:hexane as eluting solvent afforded the less polar 1α,2β,3α,4α-isomer as a white foam, $\lambda_{max}$ (ethanol) 258.2 nm ($E_1^1$ 130), 286.4 nm ($E_1^1$ 118), $^1$H nmr (DMSO-$d_6$, 60°) δ 7.1–7.5(46H), 6.81(1H), 4.8–5.05(1H), 4.91(1H), 4.33(1H), 3.92(1H), 3.45(3H), 2.93,3.08(2H) and 1.9–2.25(2H); and the more polar 1α,2α,3β,4β-isomer also as a white foam, $\lambda_{max}$(ethanol) 259.2 nm ($E_1^1$ 113), 286.6 nm ($E_1^1$ 107), $^1$H nmr (DMSO-$d_6$, 60°) δ 7.63(1H), 7.1–7.6(45H), 6.47(1H), 5.2(1H), 4.51(1H), 4.16(1H), 3.88(1H), 3.5,3.61(2H), 3.39(3H) and 2.2–2.5(2H).

INTERMEDIATE 9

(±)(1α,2α,3β,4β)-42-Amino-6-methoxy-9H-purin-9-yl-3-fluoro-1-hydroxymethylcyclopentane-1,2-diol Water (1.5 ml) was added to a solution of the 1α isomer of Intermediate 8 (473 mg) in glacial acetic acid (6 ml) and the mixture stirred at 80° for 2 h. Evaporation of the solvent and trituration of the residue with ether provided the title compound as a fawncrystalline solid (131 mg), mp 238°–242°. $^1$H nmr (DMSO-$d_6$) δ 7.9(1H), 6.48(2H), 5.46(1H), 4.6–5.2(4H), 4.16(1H), 3.97(3H), 3.3–3.5(2H), 2.5(1H) and 2.06(1H).

INTERMEDIATE 10

(±)(1'α,2'α,3'β,4'β)-9-2,4-Difluoro-3-triphenylmethoxy-4-triphenylmethoxymethyl-1-cyclopentyl-6-methoxy-2-triphenylmethylamino-9H-purine A solution of the 1α,2β,3α,4α-isomer of Intermediate 8 (156 mg) in dichloromethane (2 ml) was added dropwise over 5 min to a stirred and ice-cooled solution of diethylaminosulphur trifluoride (0.04 ml) in the same solvent (1.5 ml). After a further 15 min ice-cold aqueous sodium bicarbonate (2 ml) was added and the mixture stirred for 30 min. The organic phase was separated, dried and evaporated to a foam. Purification by preparative layer chromatography (Whatman silica) using 1:1 ethyl acetate:petrol for development afforded the title compound as a white foam (65 mg). $^1$H nmr (DMSO-$d_6$,60°) δ 7.58(1H), 7.1–7.45(45H), 6.83(1H), 4.9(1H), 4.38(1H), 3.89(1H), 3.56(3H), 3.32(1H), 2.72(1H) and 2.25–2.55(2H), $^{19}$F nmr (DMSO-$d_6$, 60°) δ −188 and −164.5.

INTERMEDIATE 11

Aristeromycin-1-oxide m-Chloroperbenzoic acid (72.3 g) was added to a solution of Aristeromycin (56 g) in 1:1 water:dioxan (3.36 ) and the mixture stirred in the dark for 20 h. The mixture was then filtered and the filtrate evaporated to leave a white solid which was washed successively with ether and methanol to afford the title compound as a white solid (49.4 g). Recrystallisation from methanol afforded white crystals, mp 145°–9°. $^1$H nmr (DMSO-$d_6$) δ 1.71,2.26(2H), 2.04(1H), 3.39–3.57(2H), 3.84(1H), 4.62–4.8(3H), 5.01(1H), 8.2(2H), 8.4(1H) and 8.61(1H).

INTERMEDIATE 12

(1R,2R,3S,4R)-2,3-Dihydroxy-4-[2-imino-1,2-dihydro[1,2,4]oxadiazolo-[3,2-i]purin-7-yl]cyclopentanemethanol.

A solution of cyanogen bromide (2.02 g) in methanol (100 ml) was added over 15 min to a stirred and cooled (−20°) suspension of Intermediate 11 (5 g) in the same solvent (300 ml) keeping the internal temperature below −10°. The mixture was allowed to warm to 10° over 3 h when the solvent was evaporated under reduced pressure below 30°. The solid residue was triturated with ether to provide the title compound as a white solid (6.39 g). Recrystallisation from methanol/ethyl acetate afforded white crystals, mp 180°–184° (dec). $^1$H nmr (DMSO-$d_6$) δ 1.74,2.33(2H), 2.1(1H), 3.4–3.6(2H), 3.87(1H), 4.36(1H), 4.5–6.3(3H), 4.94(1H), 8.99(1H) and 10.06(1H).

INTERMEDIATE 13

(6aR,8R,9S,9aR)-Hexahydro-8-[6-cyanoimino-1,6-dihydro-1-methoxy-9H-purin-9-yl]-2,2,4,4-tetrakis(1-methylethyl)cyclopenta[f]-1,3,5,2,4-trioxadisilocin-9-ol.

Triethylamine (1 ml) was added to a stirred solution of Intermediate 12 (1 g) in N,N-dimethylformamide (10 ml) and the mixture stirred for 20 min. Methyl iodide (0.5 ml) was then added and stirring continued for a further 3 h. The solution was then cooled in ice and imidazole (0.7 g) and 1,3-dichloro-1,1,3,3-tetraisopropyldisiloxane (0.9 ml) were introduced and stirring continued for a further 45 min. The mixture was then partitioned between water and ethyl acetate. The organic phase was separated, washed with water, dried and evaporated and the residue purified by silica gel chromatography (Merck Kieselgel 60) using ethyl acetate as eluting solvent to give the title compound as a white foam (0.76 g). Crystallisation from ether gave white crystals, mp 206°–210°. $^1$H nmr (DMSO-d$_6$) δ 1.05(28H), 1.7(1H), 2.19(2H), 3.75,3.92(2H), 4.1(3H), 4.3(2H), 4.68(1H), 4.90(1H), 8.44(1H) and 8.80(1H).

INTERMEDIATE 14

(6aR,8R,9S,9aR)-Hexahydro-8-[6-cyanoimino-1,6-dihydro-1-methoxy-9H-purin-9-yl]-2,2,4,4-tetrakis(1-methylethyl)cyclopenta[f]-1,3,5,2,4-trioxadisilocin-9-ol, phenoxythiocarboxylate A solution of phenyl chlorothionocarbonate (1.4 g) in dichloromethane (10 ml) was added dropwise to a stirred and ice-water cooled solution of Intermediate 13 (3 g) and 4-dimethylaminopyridine (1.3 g) in dichloromethane (20 ml). After 2 h the resulting solution was diluted with dichloromethane (10 ml) and washed successively with 1M hydrochloric acid and a saturated aqueous solution of sodium bicarbonate. The organic phase was dried and evaporated to a foam, which was purified by chromatography on silica gel (Merck Kieselgel 60) in a gradient of ethyl acetate and petrol mixtures (1:2 to 1:0). Evaporation of appropriate fractions gave the title compound as a white foam (2.9 g). $\lambda_{max}$ (ethanol) 226.3 nm (E$_1^1$313), 286.6 nm (E$_1^1$296); $^1$H nmr (CDCl$_3$) δ 8.12 (1H), 8.02(1H), 7.48–7.36(2H), 7.34–7.26(1H), 7.04–7.14(1H), 5.90–5.98(1H), 4.97(1H), 4.9–4.8(1H), 4.22(3H), 4.12–3.80(2H), 2.42–2.26(2H), 2.20–2.03(1H), 1.20–0.96(28H).

INTERMEDIATE 15

(6aR,8R,9aS)-Hexahydro-8-[6-cyanoimino-1,6-dihydro-1-methoxy-9H-purin-9-yl]-2,2,4,4-tetrakis(1-methylethyl)cyclopenta[f]-1,3,5,2,4-trioxadisilocin.

Nitrogen was passed through a solution of Intermediate 14 (2.8 g),2,2'-azobis-(2-methylpropionitrile) (132 mg) and tri-n-butyltin hydride (2.2 g) in dry toluene (30 ml). After 1 h, the solution was stirred under nitrogen and heated in an oil-bath at 76°. During the following 5 h 2,2'-azobis-(2-methylpropionitrile) (90 mg) and tri-n-butyltin hydride (1.1 g) were added in portions. After cooling, the resulting solution was diluted with ethyl acetate (20 ml) and washed successively with water, 1M hydrochloric acid, water, saturated aqueous sodium bicarbonate solution, and brine. The organic phase was dried and evaporated to a syrup. Purification by chromatography on silica gel (Merck Kieselgel 60) in a gradient of ethyl acetate and petrol (1:2 to 2:1) afforded the title compound as a white foam (1.2 g). $\lambda_{max}$ (ethanol) 223.4 nm (E$_1^1$305), 286 nm (E$_1^1$350), $^1$H nmr (CDCl3) δ 8.16(1H), 7.97(1H), 5.02(1H), 4.65(1H), 4.22(3H), 4.09–3.70(2H), 2.44–1.9(5H), 1.2–0.9(28H).

INTERMEDIATE 16

(1R,2S,4R)-4-[6-Cyanoimino-1,6-dihydro-1-methoxy-9H-purin-9-yl]-2-hydroxycyclopentanemethanol.

3M Hydrochloric acid (50 ml) was added to a stirred solution of Intermediate 15 (20 g) in 1,4-dioxan (150 ml). After 2½ h, 3M hydrochloric acid (10 ml) was added. After a further 2½ h, solid sodium bicarbonate was added to raise the pH to 6–7. The resulting mixture was evaporated to a slurry, which was dried by azeotroping with ethanol. Purification by chromatography on silica gel (Merck kieselgel 60) in a gradient of chloroform and methanol (10:1 to 1:1), gave the title compound as a white solid (4.4 g). $\lambda_{max}$ (water) 223.8 nm (E$_1^1$571), 288.0 (E$_1^1$679), $^1$H nmr (DMSO-d$_6$) δ 8.88(1H), 8.49(1H), 5.03(1H), 4.87(1H), 4.69(1H), 4.1(4H), 3.60–3.38(2H), 2.45–1.94(4H), 1.81–1.65(1H).

INTERMEDIATE 17

(1S,2S,4R)-4-[6-Cyanoimino-1,6-dihydro-1-methoxy-9H-purin-9-yl]-2-iodomethylcyclopentanol A solution of methyltriphenoxyphosphonium iodide (205 mg) in N,N-dimethylformamide (0.5 ml) was added dropwise to a stirred and ice-water cooled solution of Intermediate 16 (92 mg) in N,N-dimethylformamide (1 ml). After 15 min, the cooling bath was removed and the solution was stirred at ambient temperature. After 3 h, the resulting solution was evaporated to a syrup. Purification by chromatography on silica gel (Merck Kieselgel 60) in a gradient of chloroform and methanol (40:1 to 20:1) gave the title compound as a pale yellow solid (71 mg). $\lambda_{max}$ (ethanol) 228.4 nm (E$_1^1$371), 286.8 nm (E$_1^1$466), $^1$H nmr (DMSO-d$_6$) δ 8.90(1H, 8.48(1H), 5.19(1H), 5.07(1H), 4.10(3H), 4.04(1H), 3.6–3.3(2H), 2.5–2.04(4H), 1.84–1.66(1H).

INTERMEDIATE 18

(1S,4R)-4-[6-Cyanoimino-1,6-dihydro-1-methoxy-9H-purin-9-yl]-2-methylenecyclopentanol A stirred solution of Intermediate 17 (560 mg) in pyridine (15 ml) was heated in a oil-bath at 70°. After 1½ h the reaction mixture was evaporated to a brown syrup. Purification by chromatography on silica gel (Merck Kieselgel 60) in a gradient of chloroform and methanol (20:1 to 2:1) gave the title compound as white solid (200 mg). $\lambda_{max}$ (ethanol) 228.4 nm (E$_1^1$526), 287.2 nm (E$_1^1$677), $^1$H nmr (DMSO-d$_6$) δ 8.90(1H), 8.48(1H), 5.20–5.03(4H), 4.57(1H), 4.10(3H), 3.08–2.70(2H), 2.43–2.07(2H).

INTERMEDIATE 19

(1'R,4'S)-6-Cyanoimino-1,6-dihydro-1-methoxy-9-(3-methylene-4-trihenylmethoxy-1-cyclopentyl)-9H-purine A stirred mixture of Intermediate 18 (50 mg), triphenylmethyl chloride (97 mg) and 4A molecular sieves (500 mg) in 1,2-dichloroethane (5 ml) was heated under reflux. After 21 h the mixture was filtered and the filtrate evaporated to a syrup. Purification by chromatography on silica gel (Merck Kieselgel 60) with elution by a mixture of chloroform and methanol (40:1) gave the title compound as a yellow foam (80 mg). $\lambda_{max}$(ethanol) 286.4 nm (E$_1^1$ 383), $^1$H nmr (DMSO-d$_6$) δ 8.81(1H), 8.23(1H), 7.56–7.21(15H), 5.33(1H), 5.16(1H), 4.96(1H), 4.69(1H), 4.07(3H), 3.04–2.55(2H), 1.52–1.12(2H).

INTERMEDIATE 20

(1S,2S,4S)-and (1R,2S,4S)-4-(6-Cyanoimino-1,6-dihydro-1-methoxy-9H-purin-9-yl)-2-triphenylmethoxy-1-triphenylmethoxymethyl-cyclopentanol A solution of osmium tetroxide (550 mg) in pyridine (4 ml) was added to a stirred solution of Intermediate 19 (1.05 g) in pyridine (10 ml). After 1 h, a solution of sodium metabisulphite (1.13 g) in water (2 ml) was added. After a further 1¼ h more sodium metabisulphite (1 g) and water (5 ml) were added. After a further 1½ h the resulting black solution was decanted and evaporated to a sludge which was partitioned between water and ethyl acetate. The aqueous phase was extracted with ethyl acetate and the combined organic phases were washed with water. After drying, evaporation gave a pale yellow foam which was dissolved in 1,2-dichloroethane (30 ml). Triphenylmethyl chloride (1.1 g) and powdered 4A molecular sieves (11 g) were added and the mixture was stirred and heated under reflux. After 30 min, triethylamine (0.5 ml) was added and the mixture was filtered. The filtrate was evaporated to a syrup which was purified by chromatography on silica gel (Merck Kieselgel 60) with elution by a mixture of ethyl acetate and petroleum ether. Evaporation of appropriate fractions gave the (1S,2S,4S) title compound as a foam (831 mg), $^1$H nmr (DMSO-d$_6$) δ 8.87(1H), 8.27(1H), 7.58–7.16(30H), 5.44(1H), 4.75(1H), 4.17–4.04(4H), 3.45(2H), 2.67–2.53(1H), 2.13–2.01(1H), 1.35–1.11(2H); and the (1R,2S,4S) title compound as a foam (135 mg), $^1$H nmr (DMSO-d$_6$) δ 8.62(1H), 7.98(1H), 7.58–7.15(30H), 5.11–4.95(2H), 4.18–4.05(4H), 3.22–3.05(2H), 2.08–1.97(2H), 1.18–1.2(2H).

INTERMEDIATE 21

(1S,2S,4S)-4-(2-Amino-6-methoxyamino-9H-purin-9-yl)-2-triphenylmethoxy-1-triphenylmethoxymethylcyclopentanol A stirred mixture of 1,8-diazabicyclo[5.4.0]undec-7-ene (29 mg) and the (1S,2S,4S) isomer of Intermediate 20 (130 mg) in ethanol (3.5 ml) was heated under reflux. After 2½ h, 1,8-diazabicyclo[5.4.0]undec-7-ene (5 mg) was added. After a further 1 h the mixture was evaporated to a syrup which was purified by chromatography on silica gel (Merck Kieselgel 60) with elution by a mixture of chloroform and methanol (40:1). Evaporation of appropriate fractions gave the title compound as a foam (63 mg). $^1$H nmr (DMSO-d$_6$) δ 9.71(1H), 7.57–7.15(30H), 6.79(1H), 6.36(2H), 4.95(1H), 4.72–4.58(1H), 3.97(1H), 3.71(3H), 3.3–3.25(1H), 3.0–2.93(1H), 2.0–1.64(4H).

INTERMEDIATE 22

(1'S,3'S,4'S)-6-Cyanoimino-1,6-dihydro-9-[3-fluoro-4-triphenylmethoxy-3-triphenylmethoxymethyl-1-cyclopentyl]-1-methoxy-9H-purine An ice-water cooled solution of the (1R,2S,4S) isomer of Intermediate 20 (800 mg) in dichloromethane (10 ml) was added over 9 min to a stirred and ice-water cooled solution of diethylaminosulphur trifluoride (320 mg) in dichloromethane (10 ml). After 19 min, diethylaminosulphur trifluoride (60 mg) was added and after a further 3 min an ice-water cooled saturated aqueous solution of sodium bicarbonate (10 ml) was added. After a further 1 h the phases were separated and the aqueous phase was extracted with dichloromethane. The combined organic phases were dried and evaporated to a foam which was purified by chromatography to give the title compound as a white foam (167 mg). $^1$H nmr (DMSO-d$_6$) δ 8.62(1H), 8.15(1H), 7.45–7.15(30H), 5.23–5.07(1H), 4.34–4.16(1H), 4.08(3H), 3.60(1H), ca 3.35(1H), 2.97–2.61(2H), 2.25–1.83(4H).

INTERMEDIATE 23

3(1'S,3'S,4'S)-9-[3-Fluoro-4-triphenylmethoxy-3-triphenylmethoxymethyl-1-cyclopentyl]-N$^6$-methoxy-9H-purine-2,6-diamine A stirred solution of 1,8-diazabicyclo[5.4.0]undec-7-ene (45 mg) and Intermediate 22 (160 mg) in ethanol (5 ml) was heated under reflux. After 2¼ h, the resulting solution was evaporated to a syrup. Purification by chromatography on silica gel (Merck Kieselgel 60) with elution by a mixture of chloroform and methanol (80:1) gave the title compound as a white foam (163 mg). $^1$H nmr (DMSO-d$_6$) δ 9.73(1H), 7.45–7.15(30H), 7.14(1H), 6.34(2H), 4.83–4.68(1H), 4.23–4.05(1H), 3.71(3H), 3.61–3.48(1H), 3.05–2.91(1H), 2.70–2.5(1H), 2.1–1.83(1H), 1.7–1.52(1H), 1.13–0.99(1H).

INTERMEDIATE 24

(3S,4S,6S)-6-[6-Cyanoamino-1,6-dihydro-1-methoxy-9H-purin-9-yl]-4-1-oxaspiro[2,4]heptan-4-ol An aqueous solution of t-butyl hydroperoxide (70%) (4 ml) was added to dichloromethane (6.8 ml). The resulting mixture was dried over magnesium sulphate. The dried solution (4.1 ml) was added to a stirred solution of Intermediate 18 (2.5 g) and vanadyl acetylacetonate (23 mg) in dichloromethane (80 ml). The mixture was then heated under reflux. During the next 3½ hours, more of the t-butyl hydroperoxide solution and vanadyl acetylacetonate were added. After a further 1 hour, the mixture was filtered and a small amount of sodium sulphite was added to the stirred filtrate. The mixture was filtered and the filtrate cautiously evaporated to a syrup, which was added to stirred diethyl ether (200 ml). Filtration gave the title compound as a pale yellow solid (2.59 g). λ$_{max}$ (ethanol) 228.0 nm (E$_1^1$ 436), 287.0 nm (E$_1^1$ 536); $^1$H nmr (DMSO-d$_6$) δ 8.99 (1H), 8.50 (1H), 5.29 (1H), 5.01 (1H), 4.2–4.1 (1H), 4.1 (3H), 2.92 (2H), 2.5–2.17 (4H).

INTERMEDIATE 25

Benzoic acid,(1S,2S,4S)-4-(6-cyanoimino-1,6-dihydro-1-methoxy-9H-purin-9-yl)-1,2-dihydroxycyclopent-1-ylmethyl, ester 1,4,7,10,13-Pentaoxacyclopentadecane (2.9 g) was added to a stirred mixture of Intermediate 24 (1.99 g) and sodium benzoate (2.86 g) in dimethylformamide (35 ml). After 15 hours, dimethylformamide (25 ml) was added. After a further 48 hours the mixture was filtered and the filtrate evaporated to a brown syrup, which was combined with similar material from other experiments, and purified by chromatography on silica-gel (Merck Kieselgel 60) with elution by mixtures of chloroform and methanol. Combination of appropriate fractions gave the title compound as a foam (801 mg). λ$_{max}$(ethanol) 225.4 nm (E$_1^1$ 515), 286.0 nm (E$_1^1$ 409); $^1$H nmr (DMSO-d$_6$) δ 8.84 (1H), 8.50 (1H), 8.12 (2H), 7.67 (1H), 7.60–7.52 (2H), 5.24–5.10 (1H), 4.91 (1H), 4.49 (1H), 4.09 (3H), 2.38–2.24 (4H).

INTERMEDIATE 26

(1S,2S,4S)-4-(2-Amino-6-methoxyamino-9H-purin-9-yl)-1-hydroxymethylcyclopentan-1,2-diol 1,8-Diazaicyclo[5.4.0]undec-7-ene (0.81 ml) was added to a stirred solution of Intermediate 25 (1 g) in ethanol (30 ml). The resulting solution was heated under reflux. After 3½ hours, more 1,8-diazabicyclo[5.4.0]undec-7-ene (0.1 ml) was added. After 1 hour the solution was evaporated to a brown syrup which failed to give a solid when triturated with diethyl ether. The crude product was then purified by successive chromatography on reversed-phase silica gel (Merck LiChroprep RP-8) with elution by mixtures of acetonitrile and water, and on silicagel (Merck Kieselgel 60) with elution by chloroform-methanol mixtures. Combination of appropriate fractions gave the title compound as a white foam (311 mg). $^1$H nmr (DMSO-d$_6$) δ 9.74 (1H), 7.58 (1H), 6.50 (2H), 4.9–4.7 (3H), 4.3–4.1 (2H), 3.5–3.3 (2H), 2.15–1.95 (4H).

INTERMEDIATE 27

(1R,2S,3R,5R)-3-[6-Amino-9H-purin-9-yl]-5-[((2,3-dimethylbut-2-yl)dimethylsilyloxy)methyl]-1,2-cyclopentanediol A mixture of aristeromycin (50 g) and dimethylformamide (250 ml) was stirred at room temperature and imidazole (50 g) and then dimethylthexylsilyl chloride (10 ml) were added. Three further 10 ml portions of dimethylthexylsilyl chloride were added after 20 min, 1 h and 1.75 h. After 4 h the resulting mixture was poured into rapidly stirred water (2.5 L). The suspension was filtered and the residue washed with water (2×250 ml). The air dried solid was added to di-isopropyl ether (500 ml) and stirred for 20 min. The suspension was filtered and the residue collected, stirred with diethyl ether (500 ml) and filtered to give the title compound (49 g); $^1$H nmr (DMSO-d$_6$) δ8.13 (1H), 8.09 (1H), 7.18 (2H), 5.03–4.93 (1H), 4.76–4.60 (2H), 4.41–4.28 (1H), 3.88–3.78 (1H), 3.72–3.57 (2H), 2.28–1.70 (3H), 1.67–1.52 (1H), 0.95–0.75 (12H), 0.1 (6H).

INTERMEDIATE 28

(1R,2S,3R,5R)-3-[6-Amino-9H-purin-9-yl]-5-[((2,3-dimethylbut-2-yl)dimethylsilyloxy)methyl]-1,2-cyclopentanediol, benzoate A stirred mixture of Intermediate 27 (225 g) and n-dibutyltin oxide (139 g) in toluene (2 L) and methanol (200 ml) was heated under reflux for 1.25 h and then distilled for 0.5 h. The resulting mixture was allowed to cool for a while before being filtered, whilst still hot. The filtrate was evaporated to a solid (371 g).

A solution of benzoyl chloride (66 ml) in chloroform (60 ml) was added over 20 min to a stirred and cooled (ice-water bath) solution of the above solid (371 g) and triethylamine (86 ml) in chloroform (1.8 L). During the next two hours, benzoyl chloride (10 ml) was added in portions. Then, a saturated aqueous solution of sodium bicarbonate (650 ml) was added. After 10 min, the resulting mixture was filtered through a pad of Hyflosupercel. The residual solids were washed thoroughly with chloroform (1 L). The phases were separated and the organic phase was washed successively with a saturated aqueous solution of sodium bicarbonate (1 L) and water (2×600 ml). The combined aqueous phases were extracted with chloroform. The combined organic phases were dried over magnesium sulphate and evaporated to a solid, which was heated in boiling ethyl acetate (800 ml). After 10 min, the resulting slurry was allowed to cool and then filtered. The collected solid was washed successively with ethyl acetate (200 ml) and di-isopropyl ether (400 ml). Drying gave the title compound as a white solid (200 g); λ$_{max}$ (ethanol) 230 nm (E$_1$ $_{cm}$$^{1\%}$ 318), 260.8 nm (E$_1$ $_{cm}$$^{1\%}$ 307); $^1$H nmr (DMSO-d$_6$) δ 8.19 (1H), 8.12 (1H), 8.09–9.02 (2H), 7.72–7.63 (1H), 7.60–7.50 (2H), 7.22 (2H), 5.51–5.45 (1H), 5.36–5.27 (1H), 4.90–4.65 (2H), 3.84–3.67 (2H), 2.46–1.95 (3H), 1.66–1.52 (1H), 0.86 (3H), 0.84 (9H), 0.11 (6H).

INTERMEDIATE 29

(1R,2S,3R,5R)-3-(6-Amino-9H-purin-9-yl)-5-[((2,3-dimethylbut-2-yl) dimethylsilyloxy)methyl]-1,2-cyclopentanediol, 1-benzoate-2-phenoxythiocarboxylate A solution of phenyl chlorothionoformate (73 ml) in dichloromethane (200 ml) was added dropwise over 50 min to a stirred and cooled (ice-water bath) suspension of Intermediate 28 (225 g) and 4-dimethylaminopyridine (107 g) in dichloromethane (2 L). After 30 min, the resulting yellow solution was washed successively with saturated aqueous sodium bicarbonate solution (600 ml), 1M-hydrochloric acid (2×600 ml), water (2×600 ml) and saturated aqueous sodium bicarbonate solution (600 ml and 300 ml). The organic phase was dried over dried magnesium sulphate and then evaporated to a yellow foam. Diethyl ether (350 ml) was added, with heating, followed by a slow addition of petroleum ether (b.p. 40°–60° C.) (1 L), which resulted in the displacement of a second phase, as a syrup which soon solidified. The solid was crushed to a powder and the mixture filtered. The collected solid was washed with petroleum ether (500 ml) and dried to give the title compound as a white solid (275 g); λ$_{max}$ (ethanol) 232.2 nm (E$_1$ $_{cm}$$^{1\%}$ 339), 258.8 nm (E$_1$ $_{cm}$$^{1\%}$ 272); $^1$H nmr (DMSO-d$_6$) δ 8.29 (1H), 8.14 (1H) 8.11–8.03 (2H), 7.77–7.68 (1H), 7.65–7.55 (2H), 7.38–7.15 (5H), 6.91–6.83 (2H), 6.37–6.28 (1H), 5.83–5.76 (1H), 5.49–5.34 (1H), 3.94–3.74 (2H), 2.68–2.28 (3H), 1.68–1.54(1H), 0.86 (3H), 0.85 (3H), 0.84 (6H), 0.13 (6H).

INTERMEDIATE 30

(1S,2R,4R)-4-[6-Amino-9H-purin-9-yl]-2-[((2,3-dimethylbut-2-yl) dimethylsilyloxy)methyl]-cyclopentanol, benzoate Nitrogen was passed through a stirred solution of Intermediate 29 (275 g), tri-n-butyltin hydride (160 ml) and 2,2'-azobis-(2-methylpropionitrile) (12 g) in toluene (2 L) for 45 min. The solution was then heated (oil-bath at 75°±5° C.). After 2.25 h, the solution was cooled and evaporated to a yellow syrup. Di-isopropyl ether (500 ml) was added, followed by petroleum ether (b.p. 40°–60° C.) (650 ml). After 2 h, more petroleum ether (200 ml) was added and the mixture left at 4° C. for 16 h. Filtration then gave the title compound as a white crystalline solid (148 g); m.p. 140°–143° C.; λ$_{max}$ (ethanol) 229.8 nm (E$_1$ $_{cm}$$^{1\%}$ 328), 261.2 nm (E$_1$ $_{cm}$$^{1\%}$ 320); $^1$H nmr (DMSO-d$_6$) δ 8.22 (1H), 8.12 (1H), 8.06–7.97 (2H), 7.72–7.63 (1H), 7.61–7.50 (2H), 7.22 (2H), 5.42–5.33 (1H), 5.18–5.01 (1H), 3.86–3.69 (2H), 2.73–1.94 (5H), 1.63–1.49 (1H), 0.83(3H), 0.80 (9H), 0.09 (6H).

INTERMEDIATE 31

(1S,2R,4R)-4-(6-Amino-9H-purin-9-yl)-2-hydroxymethylcyclopentanol, benzoate

A solution of tetra-n-butylammonium fluoride in tetrahydro- furan (1 molar) (620 ml) was added to a stirred solution of Intermediate 30 (218 g) in tetrahydrofuran (1.4 L). After 1.5 h ethanol (100 ml) was added. After a further 30 min, the solution was evaporated to a slurry which was filtered. The collected solid was washed successively with ethanol (150 ml), ethanol-di-isopropyl ether (1:1) (240 ml) and di-isopropyl ether (200 ml). Drying gave the title compound as a white solid (114 g), m.p. 206°–210° C., λ$_{max}$ (ethanol) 229.8 nm (E$_1$ $_{cm}$$^{1\%}$ 430), 260.8 nm ($E_{1\ cm}^{1\%}$ 429); $^1$H nmr (DMSO-d$_6$) δ8.28 (1H), 8.14 (1H), 8.07–7.97 (2H), 7.75–7.64 (1H), 7.62–7.50 (2H), 7.22 (2H), 5.42–5.13 (1H), 5.19–5.01 (1H), 4.89 (1H), 3.70–3.55 (2H), 2.71–1.91 (5H).

INTERMEDIATE 32

(1S,2S,4R)-4-(6-Amino-9H-purin-9-yl)-2-iodomethyl cyclopentanol, benzoate

Methyltriphenoxyphosphonium iodide (219 g) was added over 5 min to a stirred and cooled (acetone-drikold bath) suspension at −62° C. of Intermediate 31 (114 g) in tetrahydrofuran (2 L). After 12 min, the cooling bath was removed and the mixture was stirred at ambient temperature. After 2 h, methanol (60 ml) was added and after a further 10 min, the resulting mixture was filtered through a pad of Hyflosupercel. The filtrate was evaporated to a brown syrup, which was stirred with diethyl ether (1 L). After 45 min, the mixture was filtered. The collected solid was stirred with di-isopropyl ether (300 ml). Methanol (300 ml) was then added. After a few min, the mixture was filtered and the collected solid was washed successively with a mixture of di-isopropyl ether-methanol (1:1) (400 ml), di-isopropyl ether (200 ml) and diethyl ether (200 ml). Drying gave the title compound as a pale yellow solid (84 g); $λ_{max}$ (methanol) 230.4 nm ($E_{1\ cm}^{1\%}$ 371), 261.0 nm ($E_{1\ cm}^{1\%}$ 366); $^1$H nmr (DMSO-d$_6$) δ 8.28 (1H), 8.15 (1H), 8.08–7.78 (2H), 7.75–7.65 (1H), 7.63–7.51 (2H), 7.29 (2H), 5.33–5.23 (1H), 5.21–5.05 (1H), 3.67–3.50 (2H), 2.83-ca. 1.95 (5H).

INTERMEDIATE 33

(1S,4R)-4-(6-Amino-9H-purin-9-yl)-2-methylenecyclopentanol, benzoate

Nitrogen was passed through a solution of Intermediate 32 (163.5 g) in pyridine (1.4 L) for 20 min. The solution was then stirred and a solution of 1,5-diazabicyclo[4.3.0]non-5-ene (49 ml) in pyridine (50 ml) was added. The resulting black solution was heated (oil-bath at 80°±3° C.). After 1 h, the resulting solution was allowed to cool and then evaporated to a syrup, which was dissolved in chloroform (600 ml). The resulting solution was washed successively with water (2×600 ml) and saturated aqueous sodium bicarbonate solution (2×300 ml) and then dried over magnesium sulphate. Evaporation gave a black syrup which was purified by chromatography on silica-gel. Elution was by mixtures of chloroform and methanol (80:1 to 20:1). Combination of appropriate fractions and then evaporation gave a foam which was crystallised from a mixture of dichloromethane and di-isopropyl ether to give the title compound as a white solid (88.5 g); m.p. 146°–148° C.; $λ_{max}$ (ethanol) 230.2 nm ($E_{1\ cm}^{1\%}$ 467), 261.0 nm ($E_{1\ cm}^{1\%}$ 469); $^1$H nmr (DMSO-d$_6$) δ 8.28 (1H), 8.15 (1H), 8.07–7.94 (2H), 7.74–7.64 (1H), 7.62–7.51 (2H), 7.24 (2H), 5.96–5.88 (1H), 5.42 (1H), 5.32 (1H), 5.29–5.14 (1H), 3.20–2.92 (2H), 2.86–2.40 (2H).

INTERMEDIATE 34

(1S,4R)-(6-Amino-9H-purin-9-yl)-2-methylenecyclopentanol

A stirred mixture of Intermediate 33 (88.5 g) and Amberlite 1RA 400 (OH) (280 g) in methanol (900 ml) was heated under reflux. After 1.75 h the mixture was allowed to cool and then filtered. The filtrate was reduced in volume and then filtered through a pad of Hyflosupercel. The filtrate was evaporated to a syrup, which was crystallised from a mixture of methanol (a few ml) and ethyl acetate (200 ml). Filtration gave the title compound as a white solid (54.6 g); m.p. 158°–163°C; $λ_{max}$ (methanol) 260.6 nm ($E_{1\ cm}^{1\%}$ 601); $^1$H nmr (DMSO-d$_6$) δ 8.20 (1H), 8.12 (1H), 7.21 (2H), 5.19 (1H), 5.13 (1H), 5.06 (1H), 4.63–4.53 (1H), 3.04–2.74 (2H), 2.48–2.02 (2H).

INTERMEDIATE 35

(1S,4R)-4-(6-Amino-9H-purin-9-yl)-2-methylenecyclopentanol,1′-oxide m-Chloroperbenzoic acid (80%) (63.53 g) was added to a stirred suspension of Intermediate 34 (54.5 g) in ethanol (1 L). After 15 min, ethanol (200 ml) was added. After a further 15 min, more ethanol (400 ml) was added. After a further 1.25 h, water (300 ml) was added. The resulting solution was filtered and the filtrate evaporated to about 300 ml. Water (200 ml) was added and evaporation of ethanol was continued. The resulting mixture was filtered and the filtrate was evaporated to a white solid which was stirred with ethyl acetate (200 ml). Filtration gave the title compound as a white solid (38 g); $λ_{max}$ (water) 232.2 nm ($E_{1\ cm}^{1\%}$ 1398), 262.0 nm ($E_{1\ cm}^{1\%}$ 285); $^1$H nmr (DMSO-d$_6$)δ 8.62 (1H), 8.18 (1H), 5.19 (1H), 5.07 (1H), 5.25–5.01 (1H), 4.62–4.52 (1H), 3.07–2.73 (2H), 2.47–2.05 (2H).

INTERMEDIATE 36

(1S,4R)-4-(2-Imino-1,2-dihydro-[1,2,4]oxadiazolo[3,2-i]purin-7-yl)-2-methylenecyclopentanol, hydrobromide A solution of cyanogen bromide (27.5 g) in methanol (200 ml) was added over 15 min to a stirred and cooled (ice-water bath) suspension of Intermediate 35 (49.56 g) in methanol (500 ml). After 2.25 h the resulting yellow solution was evaporrated. Diethyl ether (300 ml) was added and the mixture stirred. After 5 h, the diethyl ether was decanted and the solid was washed with more diethyl ether. Drying gave the title compound as a pale yellow solid (66.3 g); $λ_{max}$ (ethanol) 227.2 nm ($E_{1\ cm}^{1\%}$ 531), 286.2 nm ($E_{1\ cm}^{1\%}$ 517); $^1$H nmr (DMSO-d$_6$) δ 10.75–10.45 (2H), 10.06 (1H), 8.94 (1H), 5.38–5.23 (1H), 5.24 (1H), 5.01 (1H), 4.66–4.55 (1H), 3.15–2.76 (2H), 2.5–2.16 (2H).

INTERMEDIATE 37

(1S,4R)-4-(6-Cyanoimino-1,6-dihydro-1-phenylmethoxy-9H-purin-9-yl)-2-methylenecyclopentanol Triethylamine (52 ml ) was added to a stirred and cooled (ice-water bath) solution of Intermediate 36 (44 g) and benzyl bromide (44 ml ) in dimethylformamide (300 ml). After 10 min, the cooling bath was removed. After 2 h, the resulting yellow solution was poured into water (2.5 L) and the pH adjusted to 7 with sodium bicarbonate. The mixture was extracted with chloroform. The organic phase was washed with water (2×300 ml) and dried over magnesium sulphate. Evaporation gave a slurry, which was stirred and di-isopropyl ether (500 ml) was added. The mixture was filtered and the solids washed with di-isopropyl ether. Drying gave the title compound as a yellow solid (36.1 g ); $λ_{max}$(ethanol) 286.6 nm ($E_{1\ cm}^{1\%}$ 494); $^1$H nmr (DMSO-d$_6$) δ 8.76 (1H), 8.48 (1H), 7.64–7.54 (2H), 7.50–7.39 (3H), 5.33 (2H), 5.20 (1H), 5.08 (1H), 5.18 (1H), 5.17–5.05 (1H), 4.62–4.52 (1H), 3.08–2.95 (1H), 2.84–2.69 (1H), 2.43–2.07 (2H).

INTERMEDIATE 38

(3S,4S,6R)-6-(6-Cyanoimino-1,6-dihydro-1-phenylmethoxy-9H-purin-9-yl)-1-oxaspiro[2.4]heptan-4-ol A solution of t-butyl hydroperoxide in 2,2,4-trimethyl-pentane (3 molar) (42 ml) was added to a stirred mixture of Intermediate 37 (35 g) and vanadyl acetylacetonate (3 g) in dichloromethane (600 ml). The resulting solution was heated under reflux. During the next 1.75 h, more vanadyl acetylacetonate (1.5 g) was added. After a further 1 h, the mixture was allowed to cool and then filtered. The filtrate was evaporated to a syrup. Diethyl ether (500 ml) was added and the mixture stirred. Filtration gave a yellow solid, which was washed with diethyl ether and dried to give the title compound as a yellow solid (35.9 g); $\lambda_{max}$ (ethanol) 287.2 nm ($E_{1\,cm}^{1\%}$ 361); $^1$H nmr (DMSO-d$_6$) δ 8.78 (1H), 8.53 (1H), 7.67–7.53 (2H), 7.53–7.38 (3H), 5.33 (2H), 5.37–5.22 (1H), 5.01 (1H), 4.18–4.08 (1H), 2.92 (2H), 2.5–2.17 (4H).

INTERMEDIATE 39

(1S,2S,4S)-4-(6-Cyanoimino-1,6-dihydro-1-phenylmethoxy-9H-purin-9-yl)-1,2-dihydroxycyclopent-1-ylmethyl, benzoate 1,4,7,10,13-Pentaoxacyclopentadecane (22.7 ml) was added to a stirred mixture of Intermediate 38 (36 g), benzoic acid (23.2 g) and sodium benzoate (27.4 g) in N,N-dimethylformamide (250 ml). The mixture was heated (oil-bath at 55°±5° C.). After 1.75 h the mixture was allowed to cool and then filtered. The filtrate was evaporated to a syrup which was mixed with ethyl acetate then washed with aqueous sodium bicarbonate solution and dried over magnesium sulphate. Evaporation gave a foam which was stirred in boiling chloroform (150 ml). After cooling, filtration gave the title compound as a white solid (15.7 g); $\lambda_{max}$ (methanol) 224.8 nm ($E_{1\,cm}^{1\%}$ 653), 286.8 ($E_{1\,cm}^{1\%}$ 384); $^1$H nmr (DMSO-d$_6$) δ 8.73 (1H), 8.54 (1H), 8.07–7.98 (2H), 7.73–7.64 (1H), 7.63–7.40 (7H), 5.32 (2H), 5.27–5.11 (1H), 5.15 (1H), 4.93 (1H), 4.47 (1H), 4.30 (2H), 2.40–2.20 (4H).

INTERMEDIATE 40

(1S,2S,4S)-4-(2-Amino-6-phenylmethoxyamino-9H-purin-9-yl)-1-hydroxymethyl-1,2-cyclopentanediol Potassium hydrogen carbonate (0.84 g) was added to a stirred mixture of Intermediate 39 (4.2 g) in ethanol (80 ml) and water (8 ml), which was then heated under reflux. After 2.5 h the resulting solution was allowed to cool and then evaporated to a foam. Purification by chromatography on silica-gel, with elution by chloroform-methanol mixtures (10:1 to 1:1) gave the title compound as a white foam (2.14 g); $\lambda_{max}$ (methanol) 281.2 nm ($E_{1\,cm}^{1\%}$ 419); $^1$H nmr (DMSO-d$_6$) δ 9.78 (1H), 7.57 (1H), 7.47–7.23 (5H), 6.56 (2H), 5.00 (2H), 4.90–4.05 (5H), 3.17 (2H), 2.10–1.95 (4H).

EXAMPLE 1

(±)(1'α,2'α,3'β,4'β)-2-Amino-1,9-dihydro-9-2-fluoro-3,4-dihydroxy-4-(hydroxymethyl)cyclopentyl-6H-purin-6-one Intermediate 9 (120 mg) was heated at 85° in 2N hydrochloric acid (4.5 ml) for 1 h. The solution was evaporated and the residue suspended in water (2 ml) and the pH adjusted to 7 with 1N sodium hydroxide solution. The resulting cream crystals of the title compound were collected, washed with water and dried in vacuo (86 mg), mp 229°–232°. $^1$H nmr (DMSO-d$_6$) δ 10.61(1H), 7.72(1H), 6.5(2H), 5.44(1H), 5.05(1H), 4.98(1H), 4.85(1H), 4.62(1H), 4.15(1H), 3.4(2H), 2.5(1H) and 2.04(1H).

EXAMPLE 2

(±)(1'α,2'α,3'β,4'β)-2-Amino-1,9-dihydro-9-2,4-difluoro-3-hydroxy-4-(hydroxymethyl)cyclopentyl-6H-purin-6-one Water (0.75 ml) was added to a solution of Intermediate 10 (174 mg) in glacial acetic acid (3 ml) and the mixture stirred at 80° for 2 h. Evaporation of the solvent and trituration of the residue with ether afforded a cream solid. This material was dissolved in 2N hydrochloric acid (2 ml) and the solution heated at 80° for 2 h and then evaporated. The residue was dissolved in water (1 ml) and the pH adjusted to 6 with 1N sodium hydroxide and the solution evaporated to a cream solid. Purification by preparative high pressure liquid chromatography provided the title compound as a white crystalline solid (27 mg), mp 228°–230°. $^1$H nmr (DMSO-d$_6$) δ 10.8(1H), 7.74(1H), 6.55(2H), 5.78(1H), 5.27(1H), 5.05(1H), 4.95(1H), 4.32(1H), 3.55–3.75(2H) and 2.35–2.8(2H).

EXAMPLE 3

(1'S,3'S,4'S)-2-Amino-1,9-dihydro-9-[3,4-dihydroxy-3-hydroxymethyl-1-cyclopentyl]-6H-purin-6-one A stirred solution of Intermediate 21 (90 mg) in a mixture of glacial acetic acid and water (4:1,2 ml) was heated in an oil-bath at 85°. After 30 min, the resulting solution was evaporated and the residual solid was triturated with diethyl ether. The ethereal solution was removed by decanting. The residual white solid was dissolved in 3M hydrochloric acid (3 ml) and heated under reflux. After 3 h the solution was evaporated to a syrup which was dried by azeotroping with ethanol. The resulting solid was dissolved in water (1.5 ml) and the pH adjusted to 6–7 with 1M aqueous sodium hydroxide solution. Purification by preparative high performance liquid chromatography gave the title compound as a white solid (15 mg). $^1$H nmr (DMSO-d$_6$) 10.55(1H), 7.79(1H), 6.42(2H), 4.91(1H), 4.82–4.73(2H), 4.25(1H), 4.2(1H), 3.43–3.25(2H), 2.15–1.98(4H). $\lambda_{max}$ (water) 252.4 nm ($E_1^1$ 424).

EXAMPLE 4

(1'S,3'S,4'S)-2-Amino-9-[3-fluoro-4-hydroxy-3-hydroxymethyl-1-cyclopentyl]-4,9-dihydro-6H-purin-6-one A stirred solution of Intermediate 23 (160 mg) in a mixture of glacial acetic acid and water (4:1, 3 ml) was heated in an oil bath at 80°. After 4 h the resulting solution was evaporated to a solid, which was dried by azeotroping with ethanol. The resulting solid was triturated with diethyl ether, leaving a yellow solid. This solid was heated in refluxing 3M hydrochloric acid. After 3 h the resulting mixture was filtered and the filtrate evaporated to a gum which was dried, by azeotroping with ethanol, to a brown solid. Trituration with diethyl ether gave a light brown solid. Trituration with diethyl ether gave a light brown solid which was dissolved in water (2 ml) and the pH adjusted to 6–7 with 1M aqueous sodium hydroxide solution. Purification by preparative high performance liquid chromatography gave the title compound as a white solid (11 mg). $^1$H nmr (DMSO-d$_6$) δ 10.61(H), 7.78(1H), 6.44(2H), 5.07(1H), 5.02(1H), 4.94(1H), 4.46–4.26(1H), 3.54–3.49(2H), 2.47–2.07(4H); $^{19}$F nmr (DMSO-d$_6$+D$_2$O) δ −166.6 λ$_{max}$ (water) 252.4 nm (E$_1^1$ 596).

EXAMPLE 5

(1′S,3′S,4′S)-2-Amino-1,9-dihydro-9-[3,4-dihydroxy-3-hydroxymethyl-1-cyclopentyl]-6H-purin-6-one (a) A solution of Intermediate 26 (330 mg) in 3M-hydrochloric acid (10 ml) was stirred and heated under reflux. After 45 minutes more 3M-hydrochloric acid (5 ml) was added. After 3½ hours the resulting solution was evaporated to a white solid which was dissolved in water (3½ ml). The pH was adjusted to 6–7 with sodium hydrogen carbonate. The resulting mixture was filtered to give a residue, which was washed successively with water (1½ ml) and aqueous acetone. The wash solutions were evaporated to a solid, which was purified by chromatography on reversedphase silica-gel (Merck Li-Chroprep RP-8). Evaporation of appropriate fractions and combination with the residue, mentioned above, gave the title compound as a white solid (199 mg). λ$_{max}$ (water) 253.2 nm (E$_1^1$ 392); $^1$H nmr (DMSO-d$_6$) δ 10.6 (1H), 7.79 (1H), 6.46 (2H), 4.92 (1H), 4.78–4.25 (3H), 4.21 (1H), 3.45–3.3 (2H), 2.15–1.97 (4H).

(b) Aluminium amalgam [prepared from aluminium foil (50 mg)] was added to a stirred solution of Intermediate 26 (30 mg) in tetrahydrofuran (5 ml) and water (1 ml). After 16 hours, the mixture was filtered and the filtrate evaporated to a film which was purified by chromatography on silica-gel (Merck Kieselgel 60). To a stirred solution of the product (1.5 mg) in pH 6 phosphate buffer (0.2 ml) was added a solution of adenosine deaminase (from calf intestinal mucosa). The resulting solution was heated at 37°. After 1 hour, thin-layer chromatography indicated that the title compound had formed.

(c) A solution of adenosine deaminase (from calf intestinal mucosa) was added to a stirred solution of Intermediate 26 (0.5 mg) in pH 6 phosphate buffer (0.1 ml) at 37°. After 24 hours, thin layer chromatography showed that the title compound had formed.

EXAMPLE 6

(1′S,3′S,4′S)-2-Amino-1,9-dihydro-9-(3,4-dihydroxy-3-hydroxymethyl-1-cyclopentyl)-6H-purin-6-one A solution of Intermediate 40 (2 g) in 3M-hydrochloric acid (30 ml) was stirred and heated under reflux. During the next 2.5 h, 6M-hydrochloric acid (3 ml) was added in two portions. After a further 1.5 h, the solution was allowed to cool and then evaporated. The residual solid was treated with aqueous sodium hydroxide solution (1 molar) until the pH was 6–7. Filtration gave a solid, which was washed with water, and then recrystallised from boiling water to give the title compound as a white solid (0.71 g); m.p. 168°–176° C.; λ$_{max}$ (pH 6 buffer) 253.2 nm (E$_1$ $_{cm}^{1\%}$ 428); $^1$H nmr (DMSO-d$_6$) δ 10.54 (1H), 7.79 (1H), 6.41 (2H), 4.91 (1H), 4.81–4.72 (2H), 4.25 (1H), 4.21 (1H), 3.45–3.25 (2H), 2.16–1.98 (4H).

EXAMPLE 7

(1′S,3′S,4′S)-2-Amino-1,9-dihydro-9-(3,4-dihydroxy-3-hydroxymethyl-1-cyclopentyl)-6H-purin-6-one, sodium salt An aqueous solution of sodium hydroxide (0.1 molar) (21.97 ml) was added to a stirred suspension of Example 6 (0.62 g) in water (5 ml). The resulting solution was freeze-dried to give the title compound as a solid (0.72 g); λ$_{max}$ (pH 6 buffer) 252.4 nm (E$_1$ $_{cm}^{1\%}$ 392); $^1$H nmr (DMSO-d$_6$) δ 7.51 (1H), 4.89 (1H), 4.22 (1H), 2.17–1.95 (4H).

EXAMPLE 8

Pharmaceutical compositions (1) Topical creams

| | % w/v |
|---|---|
| (a) Sodium salt of the active ingredient | 0.25 |
| (b) Butylene glycol | 15.0 |
| (c) Glycerol | 2.5 |
| (d) Cetostearyl alcohol | 10.0 |
| (e) Self emulsifying monostearin | 1.5 |
| (f) Polyoxyethylene (2) oleyl ether | 5.0 |
| (g) Beeswax | 3.0 |
| (h) Chlorocresol | 0.1 |
| Distilled water to | 100.0 |

Heat the water to 70° and dissolve the chlorocresol (h). Melt (d), (e), (f) and (g) together, heating to 70°. Add the melt to the water with stirring. Disperse (a) in a mixture of (b) and (c) and add the dispersion (warmed to 55°) to the bulk mixture. Cool, with stirring, to 35°.

(2) Eye Ointment

| | % w/v |
|---|---|
| Sodium salt of the active ingredient | 3.0 |
| Liquid paraffin | 25.00 |
| White soft paraffin to | 100.0 |

Melt the white soft paraffin by heating to 70°. Disperse the sodium salt of the active ingredient in the liquid paraffin, warm the dispersion to 55° and add it with stirring to the molten white soft paraffin. Cool, with stirring, to 35°.

(3) Eye Drops

| | % w/v |
|---|---|
| Sodium salt of the active ingredient | 0.5 |
| Benzalkonium chloride | 0.01 |
| Sodium chloride | 0.85 |
| Water for injections to | 100.0 |

Dissolve the benzalkonium chloride, sodium chloride and the sodium salt of the active ingredient in the water. Filter the solution, collect the filtrate aseptically and fill (aseptically) into suitable sterile eye drop containers.

(4a) Oral Tablet

| | mg/Tablet | % w/w |
|---|---|---|
| Sodium salt of the active ingredient | equivalent to 100 mg active ingredient | 40.1 |
| Lactose | 100 mg | 37.2 |
| Maize starch | 50 | 18.6 |
| Polyvinyl pyrrolidone | 2 | 0.75 |
| Sodium starch glycolate | 7 | 2.6 |
| Magnesium stearate | 2 | 0.75 |

Sieve the sodium salt of the active ingredient and maize starch through a 40 mesh screen. Blend the maize starch with the lactose and the sodium salt of the active ingredient in a suitable blender. Make an aqueous solution of the polyvinyl pyrrolidone in a 5–10% w/v solution. Add this solution to the mixing powders and mix until granulated. Using suitable equipment pass the granulate through a 12 mesh screen. Dry the granules in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine. The tablets may be covered in a thin polymer coat applied by the usual film coating techniques. A pigment may be included in the film coat.

(4b) Oral Tablet

|  | mg/tablet | % w/w |
|---|---|---|
| Sodium salt of the active ingredient | equivalent to 100 mg active ingredient | 36.1 |
| Microcrystalline cellulose | 183 mg | 61.2 |
| Sodium starch glycolate | 6 mg | 2.0 |
| Magnesium stearate | 2 mg | 0.7 |

Sieve the sodium salt of the active ingredient and microcrystalline cellulose through a 40 mesh screen. Sieve the sodium starch glycolate and magnesium stearate through a 60 mesh screen. Blend the powders together in a suitable blender until homogenous. Compress on appropriate punches on an automatic tablet machine. The tablets may be covered in a thin polymer coat applied by the usual film coating techniques. A pigment may be included in the film coat.

(5) Oral Capsule

|  | mg/Capsule | % w/w |
|---|---|---|
| Sodium salt of the active ingredient | equivalent to 100 mg active ingredient | 43.3 |
| Lactose anhydrous | 126 mg | 50.7 |
| Magnesium stearate | 2 mg | 0.8 |
| Sodium starch glycolate | 13 mg | 5.2 |

Sieve all the ingredients and mix in a suitable blender. Fill into suitable size hard gelatin capsules using an automatic capsule filling machine.

(6) Oral syrup

|  | % w/v |
|---|---|
| Sodium salt of the active ingredient | 1.0 |
| Sucrose | 60.0 |
| Colour (optional) | as required |
| Flavour (optional) | as required |
| Distilled water to | 100.0 |

Dissolve the sucrose in water with the aid of heat. Cool and dissolve the sodium salt of the active ingredient and other items. Make up to volume. Fill the solution into suitable syrup containers.

(7) Powder (for external application)

|  | % w/w |
|---|---|
| Sodium salt of the active ingredient | 3.0 |
| Silicon dioxide | 2.0 |
| Maize starch to | 100.0 |

Blend the sieved sodium salt of the active ingredient, silicon dioxide and the maize starch in a suitable mechanical blender. Fill the resultant powder blend into suitable powder containers.

In the above pharmaceutical examples the active ingredient is (1'S, 3'S, 4'S)-2-amino-4,9-dihydro-9-[3,4-dihydroxy-3-hydroxymethyl-1-cyclopentyl]-6H-purin-6-one. Other compounds of the invention may be formulated in a similar manner.

We claim:

1. A compound of formula (I)

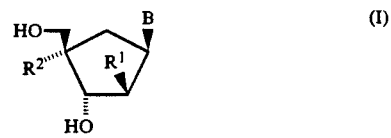

and salts and solvates thereof, in which
$R^1$ represents a hydrogen or fluorine atom or a hydroxyl group;
$R^2$ represents a fluorine atom or a hydroxyl or $C_{1-6}$alkoxy group; and B represents a purine base.

2. A compound of formula (I) as claimed in claim 1 in which B represents adenin-9-yl, guanin-9-yl, 2,6-diaminopurin-9-yl or 2-aminopurin-9-yl.

3. A compound of formula (I) as claimed in claim 1 in which B represents guanin-9-yl.

4. A compound of formula (I) as claimed in claim 1 in which B represents guanin-9-yl, $R^1$ represents a hydrogen or fluorine atom and $R^2$ represents a fluorine atom or a hydroxyl group.

5. A compound of formula (I) as claimed in claim 1 wherein $R^2$ is a hydroxyl group.

6. A compound of formula (I) as claimed in claim 3 wherein $R^2$ is a hydroxyl group.

7. A compound of formula (I) as claimed in claim 4 wherein $R^2$ is a hydroxyl group.

8. The compound of claim 1 which is (1'S,3'S,4'S)-2-amino-1,9-dihydro-9-[3,4-dihydroxy-3-hydroxymethyl-1-cyclopentyl]-6H-purin-6-one and physiologically acceptable salts and solvates thereof.

9. The compound of claim 1 which is (1'S,3'S,4'S)-2-amino-1,9-dihydro-9-[3,4-dihydroxy-3-hydroxymethyl-1-cyclopentyl]-6H-purin-6-one, sodium salt.

10. A method for the therapy or prophylaxis of Herpetoviridae infections in a human or animal subject which comprises administering an antivirally effective amount of a compound of formula (I) as defined in claim 1 or a physiologically acceptable salt or solvate thereof.

11. Pharmaceutical compositions comprising at least one compound of formula (I) as defined in claim 1 or a physiologically acceptable salt or solvate thereof in association with at least one physiologically acceptable carrier or excipient.

12. Compositions as claimed in claim 11 for oral, buccal, parenteral, topical or rectal administration.

13. Compositions as claimed in claim 11 for oral administration in a form selected from tablets, capsules, suspensions, emulsions, syrups, elixirs and suppositories.

14. Compositions as claimed in claim 11 for buccal administration in a form selected from tablets and lozenges.

15. Compositions as claimed in claim 11 for topical administration in a form selected from ointments, creams, lotions, powders, pessaries and drops.

16. Compounds of formula (II)

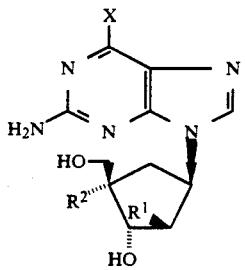

(II)

wherein $R^1$ and $R^2$ are as defined in claim 1 and X represents halogen, $NH_2$, alkoxyamino, alkoxy or phenylmethoxyamino.

17. Compounds of formula (II) as claimed in claim 16 in which X represents halogen, alkoxylamino, alkoxy or phenylmethoxyamino.

18. A pharmaceutical composition as claimed in claim 12 wherein the compound of formula (I) comprises 0.5% to 5% of the composition.

19. A method according to claim 10 wherein the compound is administered topically.

20. A method according to claim 19 wherein the antivirally effective amount is from 0.1 mg to 1000 mg per day.

* * * * *